United States Patent
Clark et al.

(10) Patent No.: US 6,491,697 B1
(45) Date of Patent: *Dec. 10, 2002

(54) METHOD AND APPARATUS FOR INSERTING A FLEXIBLE MEMBRANE INTO AN EYE

(75) Inventors: George Clark, Lewis Center, OH (US); Thomas M. Heyman, Chino Hills, CA (US)

(73) Assignee: Bausch & Lomb, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/334,183

(22) Filed: Jun. 16, 1999

Related U.S. Application Data

(62) Division of application No. 08/721,349, filed on Sep. 26, 1996, now Pat. No. 5,944,725.

(51) Int. Cl.[7] ................................. A61F 9/00
(52) U.S. Cl. ..................... 606/107; 623/6.12
(58) Field of Search ............ 606/1, 107, 108; 600/235, 236, 243; 623/4.1, 6.11, 6.12, 6.43, 6.51

(56) References Cited

U.S. PATENT DOCUMENTS

| | | |
|---|---|---|
| 4,573,998 A | 3/1986 | Mazzocco |
| 4,600,003 A | 7/1986 | Lopez |
| 4,600,004 A | 7/1986 | Lopez et al. |
| 4,619,256 A | 10/1986 | Horn |
| 4,681,102 A | 7/1987 | Bartell |
| 4,702,244 A | 10/1987 | Mazzocco |
| 4,715,373 A | 12/1987 | Mazzocco et al. |
| 4,731,079 A | 3/1988 | Stoy |
| 4,747,404 A | 5/1988 | Jampel et al. |
| 4,750,498 A | 6/1988 | Graham |
| 4,763,650 A | 8/1988 | Hauser |
| 4,765,329 A | 8/1988 | Cumming et al. |
| 4,822,360 A | 4/1989 | Deacon |
| 4,834,094 A | 5/1989 | Patton et al. |
| 4,836,201 A | 6/1989 | Patton et al. |
| 4,836,202 A | 6/1989 | Krasner |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,950,289 A | 8/1990 | Krasner |
| 4,957,505 A | 9/1990 | McDonald |
| 4,993,936 A | 2/1991 | Siepser |
| 5,098,439 A | 3/1992 | Hill et al. |
| 5,123,905 A | 6/1992 | Kelman |
| 5,190,552 A | 3/1993 | Kelman |
| 5,275,604 A | 1/1994 | Rheinish et al. |
| 5,292,324 A | 3/1994 | McDonald |
| 5,304,182 A | 4/1994 | Rheinish et al. |
| 5,425,734 A | 6/1995 | Blake ........................ 606/107 |
| 5,474,562 A * | 12/1995 | Orchowski et al. ......... 606/107 |
| 5,494,484 A | 2/1996 | Feingold |
| 5,496,328 A | 3/1996 | Nakajima et al. |
| 5,499,987 A | 3/1996 | Feingold |
| 5,549,614 A | 8/1996 | Tunis |
| 5,562,676 A * | 10/1996 | Brady et al. ................. 606/107 |
| 5,578,042 A | 11/1996 | Cumming |
| 5,582,613 A | 12/1996 | Brady |
| 5,776,138 A * | 7/1998 | Vidal et al. .................. 606/107 |
| 5,944,725 A * | 8/1999 | Cicenas et al. ............. 606/107 |

* cited by examiner

*Primary Examiner*—Glenn K. Dawson
(74) *Attorney, Agent, or Firm*—Fitzpatrick, Cella, Harper & Scinto

(57) ABSTRACT

An instrument for inserting a flexible intraocular lens or other flexible membrane into an eye which includes a compressor for laterally compressing the lens into a small cross-sectional configuration to pass the lens through a narrow incision. The compressor includes retainers along the interior of the inserter to maintain the side edges of the lens in a substantially planar orientation during compression. The retainers preferably extend through the inserter to hold the lens during advancement toward the eye to prevent an uncontrolled rotation of the lens. A haptic guide may be placed through the distal end of the inserter to properly position the leading loop haptic of the lens.

2 Claims, 8 Drawing Sheets

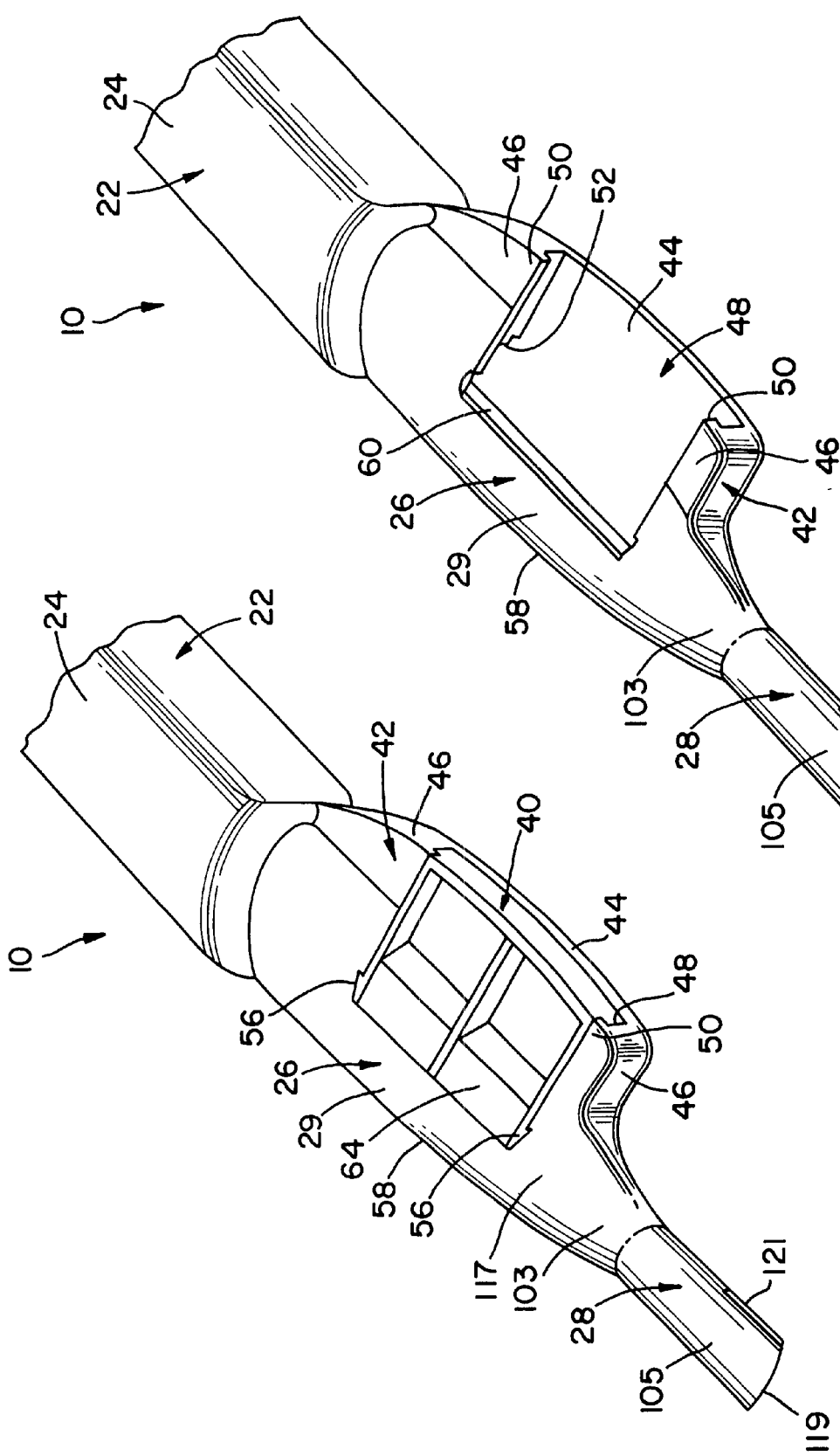

METHOD AND APPARATUS FOR INSERTING A FLEXIBLE MEMBRANE INTO AN EYE

This application is a division of application Ser. No. 08/721,349, filed Sep. 26, 1996, now U.S. Pat. No. 5,944,725.

FIELD OF THE INVENTION

The present invention pertains to a method and apparatus for inserting a flexible intraocular lens or other flexible membrane into an eye.

BACKGROUND OF THE INVENTION

The natural crystalline lens of the eye plays a primary role in focusing light onto the retina for proper vision. However, vision through the natural lens may become impaired due to an injury, or due to the formation of a cataract caused by aging or disease. To restore vision, the natural lens is typically replaced with an artificial lens. An artificial lens may also be implanted to make a refractive correction.

Many surgical procedures have been developed for removing the natural lens. Typically, a slender implement is inserted through a small incision in the eye to contact the natural lens. The implement includes a cutting tip that is ultrasonically vibrated to emulsify the lens. The emulsified fragments of the lens are then aspirated out of the eye through a passage provided in the cutting tip. The slender nature of the implement enables extraction of the lens through a small incision in the eye. The use of a small incision over other procedures requiring a large incision can lessen the trauma and complications experienced during the surgery and postoperatively.

Because the incision required to remove the lens is small, the development of intraocular implants to replace the lens has been in the direction of flexible implants that do not require any enlargement of the incision. An intraocular lens commonly includes a generally disk shaped optic which focuses Light on the retina and an outwardly extending haptic portion for proper positioning of the optic within the eye. The flexible nature of the lens enables the lens to be folded and compressed so as to occupy a smaller cross-sectional area for passage through the narrow incision and into the eye. Once inserted through the incision, the lens is permitted to expand to its original size and shape.

A number of devices have been developed to insert a flexible intraocular lens through a small incision in the eye. For example, U.S. Pat. No. 4,681,102 to Bartell uses a hinged cartridge which closes about a lens to fold the lens into a narrower configuration. The cartridge is placed into an inserter mechanism which advances the folded lens into the eye. The inserter, however, requires several components to be manipulated and assembled during the operation. U.S. Pat. No. 5,275,604 to Rheinish et al. pushes the lens through a narrowing lumen formed with grooves which act to fold the lens into a smaller size as it is pushed toward the eye. The manufacture of spiraling grooves in a tapering lumen is difficult if not impossible to accomplish in a practical manner. In U.S. Pat. No. 5,304,182 to Rheinish et al., a curling member is shifted laterally to fold the lens into a size small enough to pass through the narrow incision. However, no locking arrangement is provided to ensure completely closing of the curling member.

Moreover, while these devices function to reduce the cross-sectional size of the lens for insertion into the eye, they all require the opposing side edges of the lens to be folded over on themselves in order to fit through the narrow incision. As a result, the lens must swing open within the eye to regain its original shape and size. Such unfolding causes the lens, and particularly the haptics, to be swung in an arc, and thus risks damaging the interior of the eye.

As the lens is released into the eye, the resiliency of the lens causes the lens to open and resume its natural shape. However, the folding and pressing of the lens needed to pass the lens through the small incision places a significant amount of inward pressure on the lens. As a result, the lens is frequently discharged from the inserter with considerable force and velocity. This forceful, uncontrolled release of the lens also places the interior of the eye at risk of being injured.

Further, many inserters do not maintain control of the orientation of the lens as the lens is advanced into the eye. Consequently, the lens may rotate or turn about a longitudinal axis as it is pushed through the inserter. Most lenses, however, are made to be set within the eye in a specific orientation. Accordingly, such turning of the lens can result in the lens being placed in the eye in an improper orientation.

SUMMARY OF THE INVENTION

The present invention pertains to a method and apparatus for inserting a flexible intraocular lens or other flexible membrane into an eye without the above-noted risks associated with inserter devices of the past. More specifically, the present inserter maintains the substantially planar orientation of the opposing side edges of the lens as the lens is laterally compressed into a smaller cross-sectional configuration for insertion through a narrow incision in the eye. Since the side edges of the lens are not folded over on themselves during compression, the lens does not swing open within the eye in order to regain its original shape. As a result, the risk of a part of the lens striking and injuring an interior portion of the eye after release of the lens from the inserter is reduced.

In the preferred construction, retainers in the form of troughs are formed along the interior of the inserter to receive and maintain the side edges of the lens in a substantially planar orientation during compression. The troughs further extend through the inserter to hold the lens during advancement toward the eye to prevent an uncontrolled rotation of the lens. In this way, the lens is assured of being discharged in its proper orientation.

In another aspect of the invention, the inserter permits the lens to expand prior to its release into the eye. In this way, the resilient force which works to expand the compressed lens is dissipated prior to the lens being discharged from the inserter. The lens can thus be implanted into the eye in a controlled manner.

BRIEF DESCRIPTION OF THE DRAWINGS

FIG. 2 is a partial perspective view of the instrument with a compressor in a closed position.

FIG. 3 is a partial perspective view of the instrument with the compressor removed.

DETAILED DESCRIPTION OF THE PREFERRED EMBODIMENTS

Figure 1:
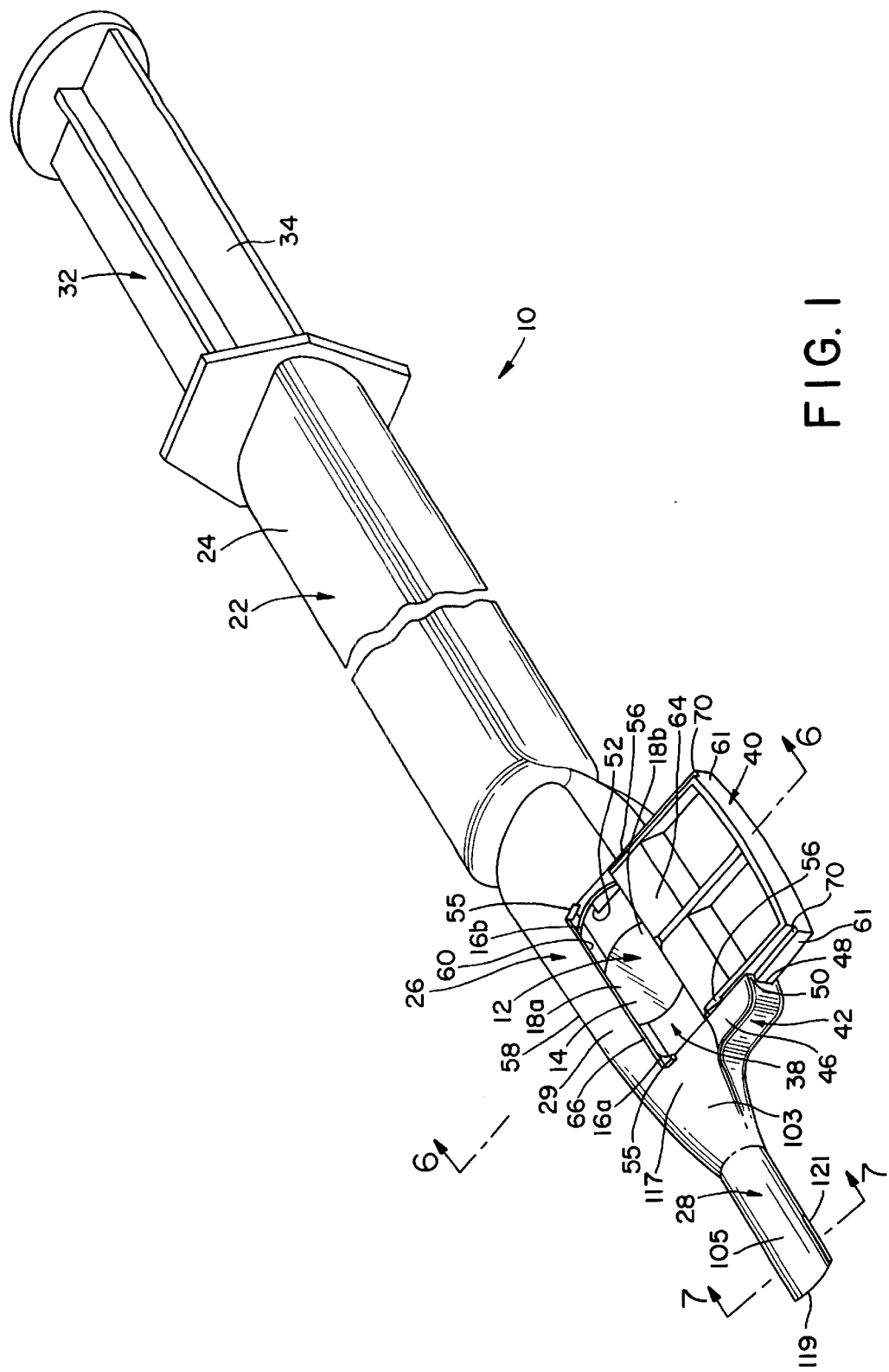
FIG. 1 is a perspective view of an instrument in accordance with the present invention.

The present invention pertains to an inserter 10 (FIGS. 1–7) for implanting a flexible intraocular lens or other flexible membrane into an eye. An intraocular lens typically includes an optic and a haptic portion, although the haptic portion is occasionally omitted. The haptic portion can take many forms, but is usually composed of plate or loop haptics. For illustration purposes only, this application will describe the use of inserter 10 with a lens 12 provided with a pair of loop haptics 16a, 16b (FIGS. 1, 5, 6, 8 and 10). Inserter 10, however, is usable with a wide variety of lenses or other flexible membranes.

Lens 12 includes an optic 14 and a pair of loop haptics 16a, 16b (FIGS. 1, 5, 6, 8 and 10). The haptics are thin, wire-like, resilient members which extend from diametrically opposed sides 18a, 18b of optic 14 in opposite directions. Haptics 16a, 16b are arcuate in shape such that their free ends 20 point generally back toward optic 14.

In the preferred construction, inserter 10 includes a tubular member 22 for receiving and directing the lens into an eye (FIGS. 1–3 and 5–7). The tubular member 22 generally includes a body 24, a compressing station 26, and a cannula 28 (FIGS. 1–3 and 5). Body 24, cannula 28, and a support portion 29 of compressing station 26 are preferably formed as a unitary molded member, although an integral assembly of plural parts could also be used.

At the proximal end of member 22, body 24 forms a rearwardly opening passage which is adapted to receive a plunger 32 (FIG. 1). The plunger includes a base 34 matingly received in body 24 and a shaft 36 (FIG. 10) which extends forward to engage and push lens 12 into an eye. As is known in the industry, the base of plunger 32 is shaped to prevent rotation of the plunger relative to tubular member 22. For example, the base 34 and the passage may have complementary non-circular shapes or a key and keyway construction. In addition, while plunger 32 is preferably advanced manually through body 24, a motor or other driving arrangement could be used to move the plunger.

Compressing station 26 includes an opening 38 in axial alignment with the passage of body 24 for receiving, compressing and directing lens 12 into cannula 28 (FIGS. 1–6D). Compressing station 26 includes a support 29 molded with body 24 and cannula 28, and a compressor 40 which is mounted for movement in the support. Support 29 includes a generally U-shaped wing 42 provided with an elongate shelf 44 and a pair of arms 46. The arms and shelf collectively define a lateral channel or guideway 48 into which compressor 40 is moveably received. A lip 50 formed along the free end of each arm 46 retains compressor 40 against shelf 44 and thereby restricts the compressor to a lateral motion in channel 48. The inner end of each lip 50 defines a shoulder 55 over which a latch 56 from compressor 40 is received to lock the compressor in place for the operation. An additional abutting flange (not shown) or other known construction may also be included to prevent compressor 40 from being removed from channel 48.

Figure 4:
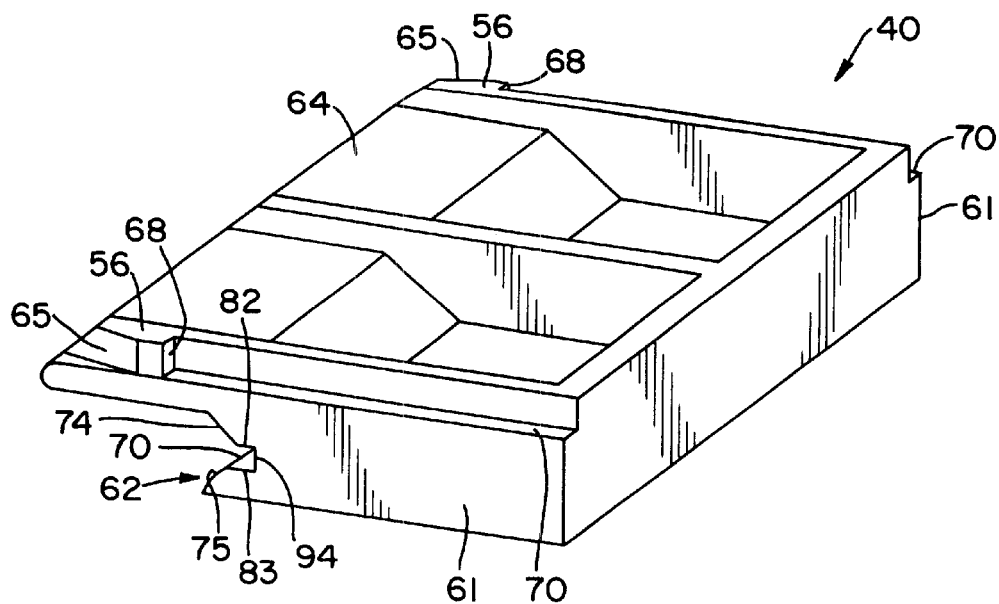
FIG. 4 is a perspective view of the compressor.
Figure 5:
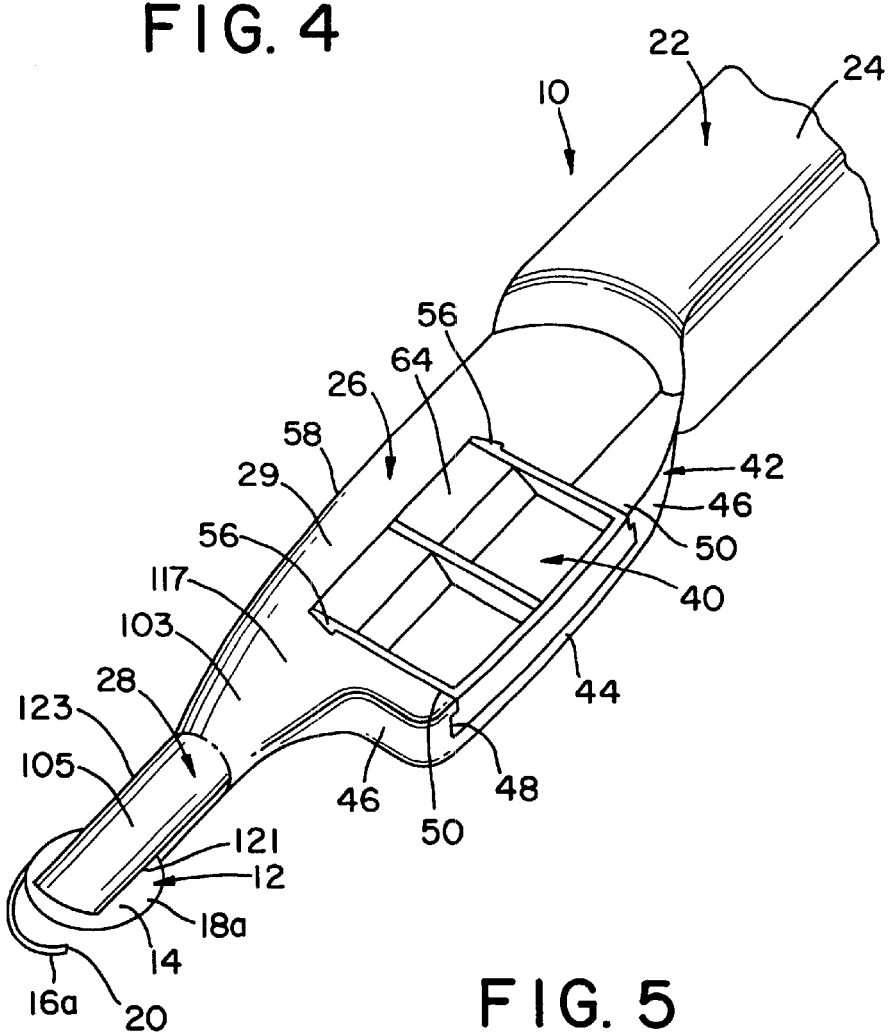
FIG. 5 is a partial perspective view of the instrument with an intraocular lens at the free end of the instrument.

Compressor 40 includes a pair of side faces 61 which are adapted to be matingly received within channel 48, and an inner sidewall 62 which is adapted to engage and compress the lens 12. A cover flange 64 projects beyond sidewall 62 to overlie the opposite side 58 of support 29 and enclose opening 38 when the compressor is moved inward (FIGS. 2 and 5–6D). Latches 56 are positioned along each side of compressor 40 above cover flange 64. Latches 56 have ramps 65 which ease the inward movement of the compressor, and abutting faces 68 which snap out to engage shoulders 55 and lock compressor 40 in its closed position with support 29. The compressor is preferably irrevocably locked in place for a single use, but could be constructed to permit release if desired. Ledges 70 underlie lips 50 to guide the lateral movement of compressor 40 within channel 48 (FIGS. 1 and 4).

Compressor 40 is laterally movable between an open position wherein cover flange 64 is spaced from side 58 of support 29 (FIG. 1), and a closed position wherein cover flange 64 overlies side 58 and latches 56 engage shoulders 55 (FIGS. 2, 5, 6C and 6D). In the open position, a gap 66 is defined between cover flange 64 and side 58 for the placing of a lens 12 into opening 38 (FIG. 1). The lens can be placed within tubular member 22 prior to shipment or by medical personnel at the time of surgery. In the closed position, sidewall 62 of compressor 40 is placed into an opposed relation with a sidewall 60 of side 58, and in axial alignment with the inner ends 52 of arms 46 (FIGS. 2, 5, 6C and 6D).

Each sidewall 60, 62 is provided with a retainer which receives and holds the opposite side edges 18a, 18b of optic 14 to prevent the side edges from being folded over or turning when compressor 40 is moved to its closed position (FIGS. 4 and 6A–6D). More specifically, the side edges 18a, 18b of the lens are oriented generally along a central plane. The retainers function to hold and support the side edges of the lens in this generally planar relationship during compression of the lens. Since the side edges of the lens are not folded over on themselves, the lens expands laterally within the eye without a swinging motion. This lateral shifting of the side edges for expansion of the lens is safer and less likely to contact and damage the interior of the eye than a swinging motion to unfold the lens. In the preferred construction, retainers are formed as troughs 68, 70. Nevertheless, the retainers could have other constructions so long as they maintain the sides of the lens in a substantially planar orientation and permit advancement of the lens into the eye.

Troughs 68, 70 are preferably flanked by inclined segments 72–75 which support and compress the optic during inward movement of compressor 40, and which help maintain the sides of lens 12 in troughs 68, 70 (FIGS. 6A–6D). Sidewalls 60, 62 are spaced apart by upper and lower parallel surfaces defined by cover flange 64 and shelf 44 to form an axial passage 76 through which the lens is advanced by plunger 32.

Figure 6A:
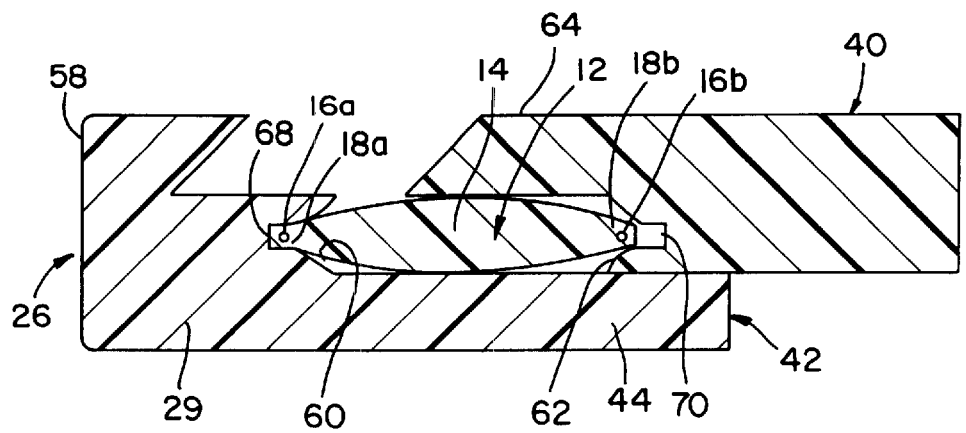
FIGS. 6A–6C are cross sectional views of the instrument taken along line 6—6 in FIG. 1 with the compressor at different stages of compressing a lens.
Figure 6B:
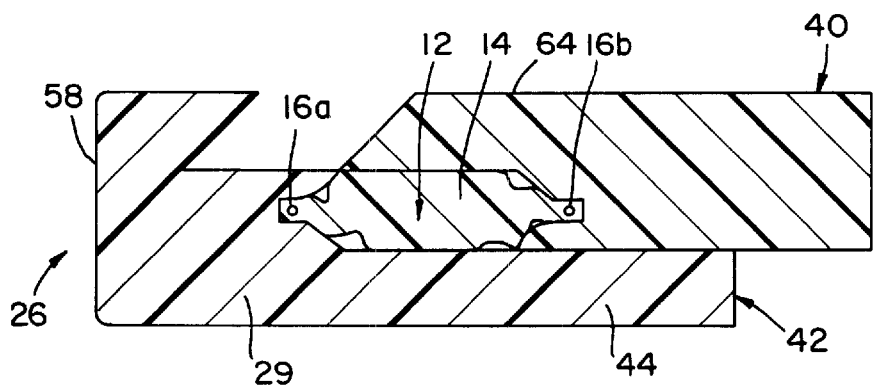
Figure 6C:
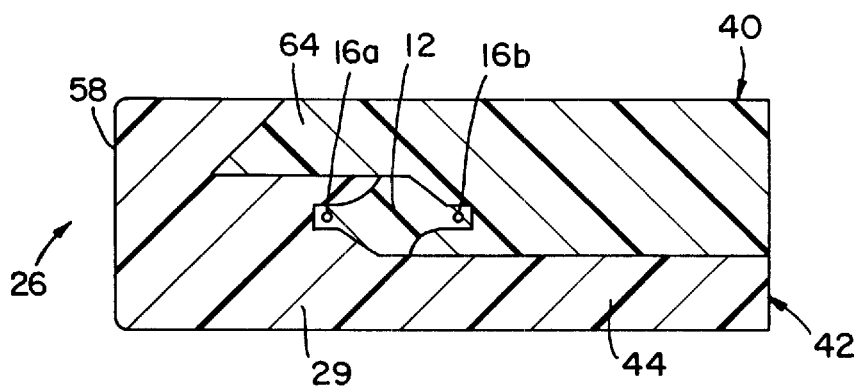

As compressor 40 is moved inward, the side edges 18a, 18b of optic 14 are received within troughs 68, 70 (FIG. 6A). Continued inward movement of the compressor causes the sides 18a, 18b to be snugly pushed into troughs 68, 70 in order to prevent their release (FIG. 6B). This movement of compressor 40 also begins to laterally compress the lens. Although the lens will have a tendency to crumple slightly during compression, side edges 18a, 18b of the lens are retained in troughs 68, 70 to maintain the edges 18a, 18b in a generally planar relationship. Finally, when latches 56 are locked on shoulders 55, lens 12 is in a compressed configuration between sidewalls 60, 62 (FIG. 6C). Inner ends 52 of arms 46 (FIG. 3) are also formed with surfaces which are identical to sidewall 62 to form continuous walls for passage 76 (FIG. 6D).

Figure 6D:
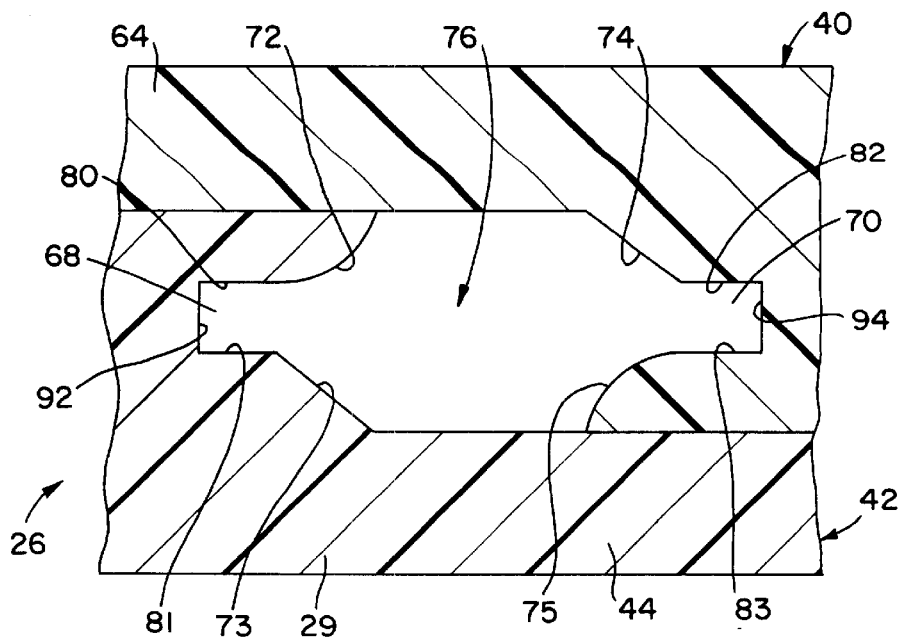
FIG. 6D is a partial cross sectional view of the instrument taken along line 6—6 in FIG. 1 with the compressor in a closed position and the lens omitted.

While flanking segments 72–75 can be identical mirror images to one another (see troughs 68a, 70a and segments 72a–75a of FIG. 8), they are preferably asymmetrical to better orient the haptics for insertion (FIG. 6D). More specifically, troughs 68, 70 are each partially defined by upper and lower faces 80–83. One face 80, 83 of each trough 68, 70 extends inward a greater distance than the opposing face 81, 82. The longer faces 80, 83 merge with arcuate flanking segments 72, 75. The shorter faces 81, 82 terminate and intersect flanking segments 73, 74 at points closer to the outer faces 92, 94 of troughs 68, 70. While the intersections of faces 81, 82 with flanking segments 73, 74 are preferably angular, they may also be rounded. In this particular construction, side edge 18a with leading haptic 16a is placed adjacent sidewall 60.

As compressor 40 is moved inward, the side edges 18a, 18b will be received into troughs 68, 70 (FIGS. 6A–6D). As lens 12 compresses, the asymmetric faces 80–83 will cause the lens to dip slightly about the shorter faces 81, 82, and create a slight twist in optic 14 so that leading haptic 16a tends to point in a downward direction. This downward orientation of leading haptic 16a will enable the surgeon to more easily place the haptic within the capsular bag of the eye. Similarly, the trailing haptic 16b is shifted to incline slightly upward to avoid contact by plunger 32; that is, so that the free end 77 of shaft 36 directly engages optic 14 (FIG. 10).

Figure 9:
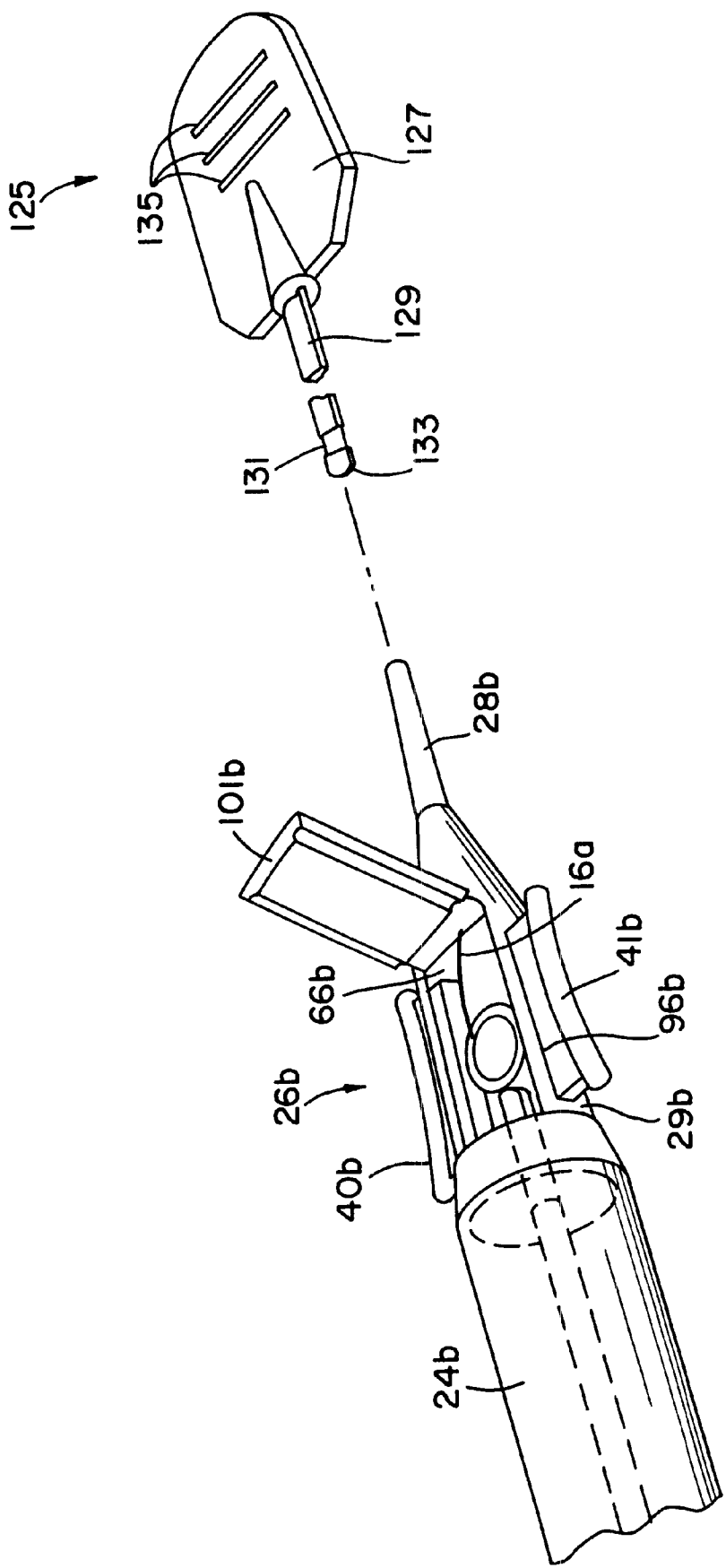
FIG. 9 is a partial perspective view of a third embodiment of an instrument in accordance with the present invention.
Figure 10:
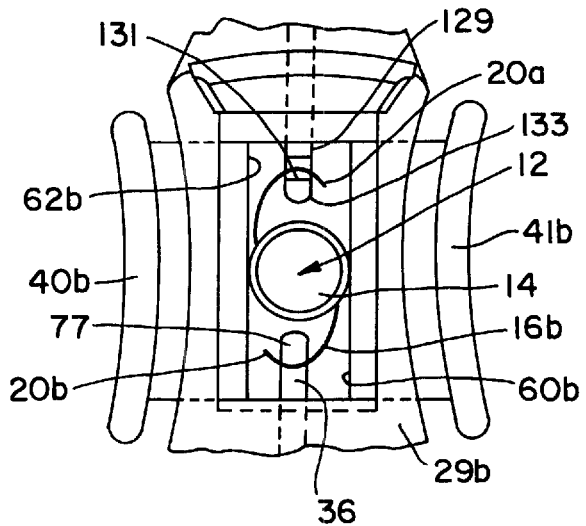
FIG. 10 is a partial top plan view of the third embodiment of the instrument.

Alternatively, compressing station 26b includes a support 29b molded with body 24b and cannula 28b, and a pair of opposed compressors 40b, 41b (FIGS. 9 and 10). The compressors are supported in a pair of opposite slits 96b formed in the sides of support 29b for lateral movement toward and away from each other. Compressors 40b, 41b have inner sidewalls 60b, 62b which are preferably shaped as described above for sidewalls 60, 62; nevertheless, the sidewalls could be symmetrically formed as with sidewalls 60a, 62a. An opening 66b is formed in the top of support 29b to permit the placement of a lens 12. To prevent loss or outward bowing of the lens, a cover 101b is hinged to support 29b to overlie opening 66b before closure of compressors 40b, 41b. Latches (not shown) are provided to lock the compressors in their closed positions.

Cannula 28 projects forwardly from the distal end of compressing station 26 to direct lens 12 into an eye (FIGS. 1–3 and 5). Cannula 28 preferably includes a proximal, funnel-shaped portion 103 which tapers to further compress the lens, and an elongate distal portion 105 which directs the compressed lens into an eye. Nevertheless, the cannula could be formed to have a uniform taper across its length or provided with no taper if, for example, the compressor(s) has a longer stroke to complete the desired compression of the lens.

Figure 7:
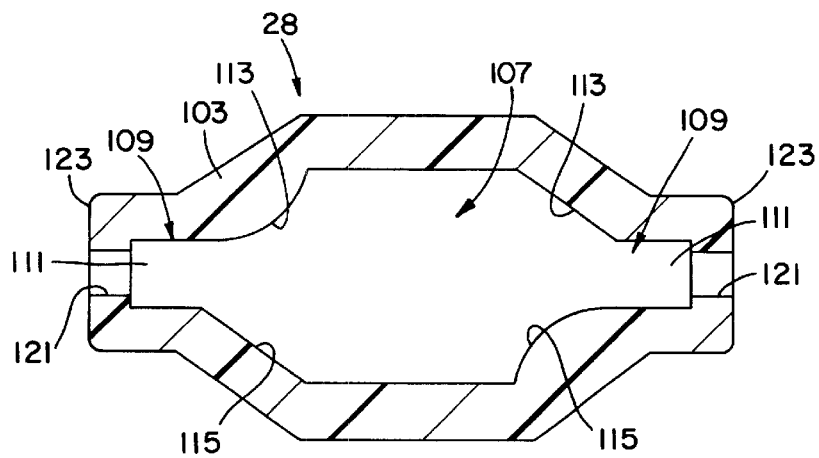
FIG. 7 is a cross-sectional view taken along line 7—7 in FIG. 1.
Figure 8:
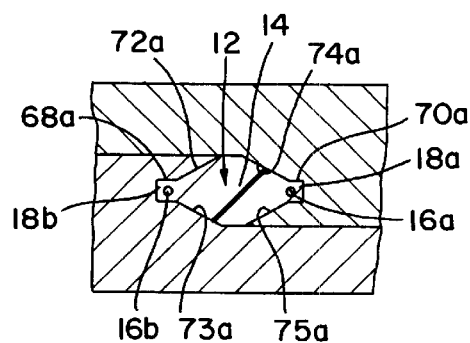
FIG. 8 is a partial cross-sectional view of a second embodiment of an instrument in accordance with the present invention illustrating the compression of a lens.

An interior lumen 107, which extends through cannula 28, is axially aligned with passage 76 of compressing station 26 to form a continuous duct through which lens 12 is moved (FIG. 7). Lumen 107 is preferably defined by sidewalls 109 provided with troughs 111 and upper and lower flanking segments 113, 115 to match sidewalls 60, 62 of compressing station 26. At the rear end 117 of proximal portion 103, troughs 111 are aligned with troughs 68, 70 (when compressor 40 is in the closed position) to form a continuous retention of side edges 18a, 18b as the lens is advanced into the eye. The sidewalls 109 of proximal portion 103 preferably converge forwardly at an angle of about 7° to further compress the lens as it is advanced through cannula 28. As noted above, troughs 111 continue to hold the side edges 18a, 18b of optic 14 as the lens passes through cannula 28 to maintain the generally planar orientation of the side edge of the lens and to prevent turning of the lens during its advancement through lumen 107.

Distal portion 105 of cannula 28 is an elongate, slender tube to permit entry of the inserter 10 through a narrow incision (not shown). While the sidewalls 109 in distal portion 105 are angularly oriented to the sidewalls 109 in proximal portion 103, they are identical with respect to the formation of the troughs 111 and flanking segments 113, 115. Troughs and flanking segments therefore continue through distal portion 105 to properly support and hold lens 12 throughout its passage through cannula 28. Although the sidewalls 109 in distal portion 105 preferably converge slightly for molding purposes, they could be formed. with parallel walls.

The free end 119 of cannula 28 is preferably provided with a pair of opposed longitudinal slits 121 in troughs 111 (FIGS. 1–3, 5 and 7). Slits 121 are wide enough to permit sides 18a, 18b of optic 14 to extend outward beyond the exterior sides 123 of cannula 28. The slits therefore permit lateral expansion of the lens prior to its release into the eye. As a result, the natural resilient force which biases the lens to assume its original uncompressed shape is dissipated in the controlled environment of the cannula. The lens is thus not released with any velocity as in many prior art inserters.

Further, since the lens is compressed without folding the side edges over on themselves, expansion of the lens requires only an outward, lateral movement of the lens. The lens experiences no swinging of the optic or haptics within the eye which risks damaging the interior of the eye. Slits 121 also continue to hold optic 14 and prevent turning of the lens so that implantation of the lens in the proper orientation is ensured. Accordingly, insertion of the lens with inserter 10 provides a safer implantation procedure than heretofore realized.

A haptic guide 125 is optionally provided in the front of inserter lob (or 10) to ensure the proper positioning of the leading loop haptic 16a (see FIGS. 9 and 10). Haptic guide 125 includes a generally flat pull tab 127 and a slender rod 129 projecting from the pull tab. Rod 129 is sized to be received rearwardly within lumen 107 from free end 119. A hook 131 or other shoulder element is formed on the free end 133 of rod 129. In use, rod 129 is fully inserted into lumen 107 so that hook 131 is visible through the gap 66b in compressing station 26b. As the lens is loaded into the opening, leading haptic 16a is looped over hook 131. Pull tab 127 is manually pulled forward to remove rod 129 from inserter 10. Removal of haptic guide 125 can be performed before or after closure of compressors 40b, 41b or cover 101b. As the rod moves forward, hook 131 engages and pulls haptic 16a forward so that its free end is positioned into lumen 107. This pulling of the haptic tends to partially straighten haptic 16*a* to point generally in the direction of the lens' movement. This positioning of the haptic reduces the risk of the leading haptic 16*a* being drawn back and becoming lodged around the optic during insertion. Ribs 135 or other gripping surface are preferably formed on pull tab 127 to enhance the manual grasping of the component.

Figure 11:
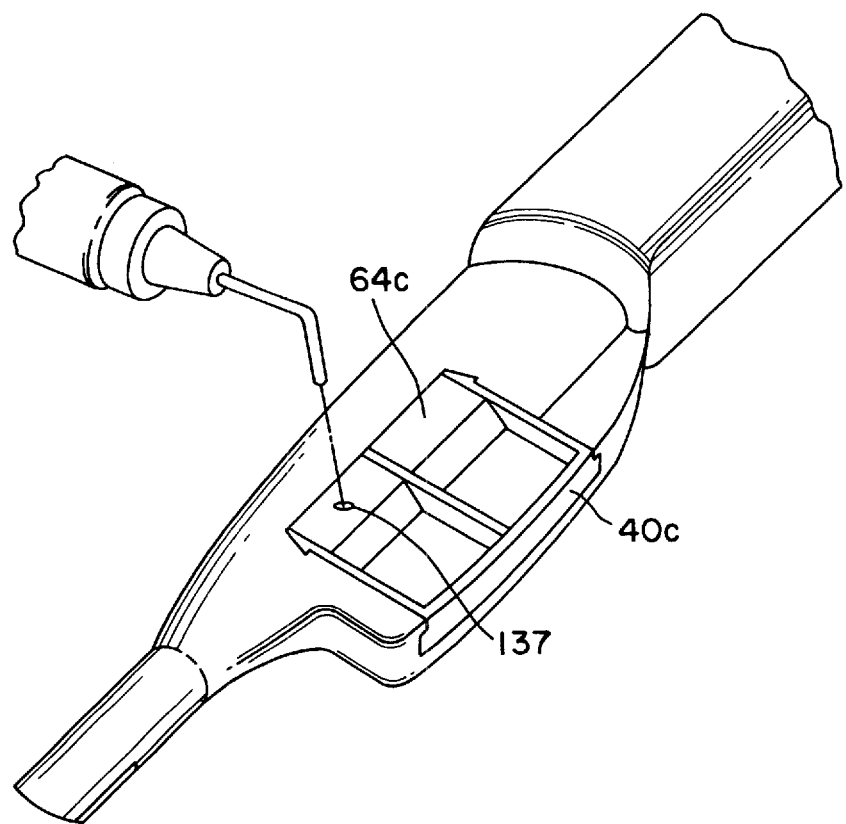
FIG. 11 is a partial perspective view of a fourth embodiment of an instrument in accordance with the present invention.
Figure 12:
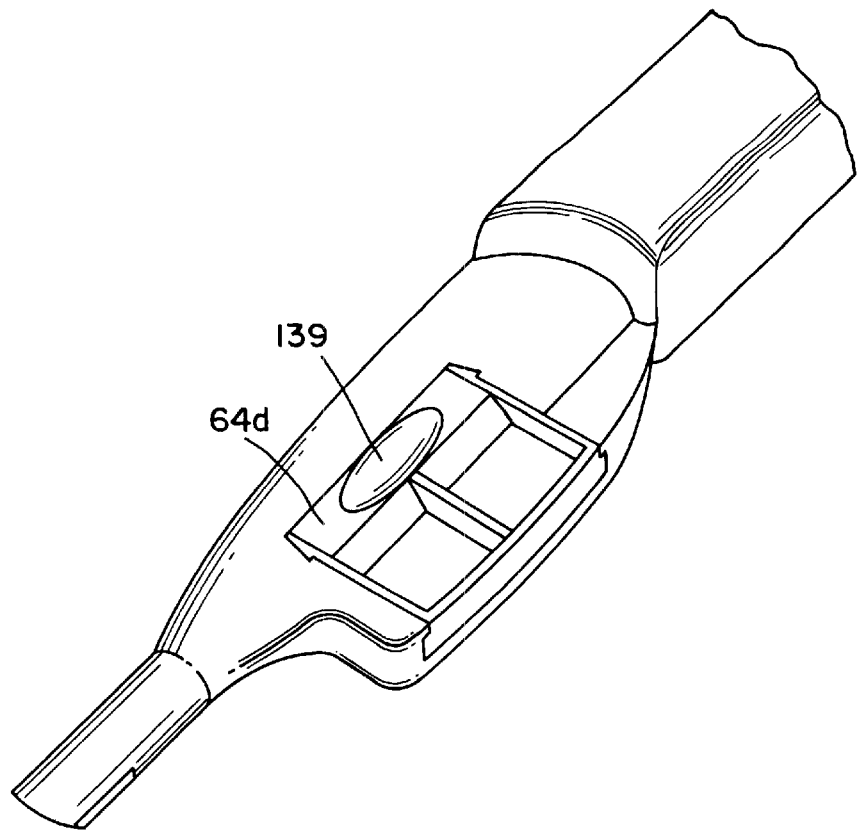
FIG. 12 is a partial perspective view of a fifth embodiment of an instrument in accordance with the present invention.
Figure 13:
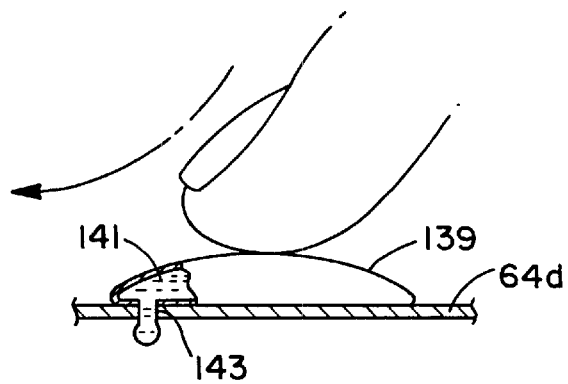
FIG. 13 is a partial cross-sectional view of the fifth embodiment of the instrument.

As is common with lens insertion procedures, a viscoelastic or other lubricant material is injected into the inserter to ease the movement of the lens into the eye. The lubricant can be injected prior to closure of compressor 40 (or cover 101*b*). Alternatively, cover flange 64*c* (or a wall of the tubular member) can be provided with an aperture 137 through which the lubricant can be injected after the closing of compressor 40*c* (FIG. 11). Also, a lubricant pouch 139 filled with a lubricant 141 can be attached to the exterior of cover flange 64*d* (FIGS. 12 and 13). A barb can be provided adjacent the aperture to puncture the plastic pouch to permit release of the lubricant into the passage upon the application of pressure on the pouch. Alternatively, pouch 139 includes a frangible portion (e.g., by scoring) which is aligned with a small aperture 143 in cover flange 64. Once the compressor is moved to its closed position, a user may apply pressure to lubricant pouch 139 to break open the pouch and dispense the lubricant into opening 38 through aperture 143. Also, cover flange 64*c* can cooperate with a fixed cutter (not shown) to open pouch 139 upon the closure of compressor 40*c* to permit the discharge of the lubricant through aperture 143 and into the passage.

The above discussion concerns the preferred embodiments of the present invention. Various other embodiments as well as many changes and alterations may be made without departing from the spirit and broader aspects of the invention as defined in the claims. For example, the compressing station, with or without the cannula, can be formed as a separable cartridge for compressing the lens. The cartridge can then be placed within an injector device for insertion of the lens into the eye after the lens has been compressed. As is common with cartridges, flanges or other structures could be included to facilitate manipulation of the cartridge and prevent turning of the cartridge in the injector device. Also, the central portion of the optic 14 could be manipulated into a U-shape, W-shape, or other folded configuration as opposed to the direct compression of the preferred embodiment. So long as the side edges of the lens are maintained in a generally planar orientation the lens will still expand with a lateral shifting motion which avoids the broad swinging of the outer edges and haptics within the eye.

What is claimed is:

1. An instrument for inserting a lens into an eye, the lens including an optic, a leading haptic and a trailing haptic, said instrument comprising a tubular unit including a passage having a distal opening through which the lens is directed into the eye, and a haptic guide including a rod received within said passage through said distal opening, said rod having an end to engage the leading haptic, said end being movable in said passage toward said distal opening and said end at least partially straightening the leading haptic during engagement of said end with the leading haptic and with movement of said end in the direction of advancement of the lens, wherein said end has having a shoulder to engage and pull the leading haptic in said passage.

2. An instrument in accordance with claim 1 in which said haptic guide further includes a pull tab for manual grasping and pulling said haptic guide from said passage.

* * * * *

UNITED STATES PATENT AND TRADEMARK OFFICE
CERTIFICATE OF CORRECTION

PATENT NO.    : 6,491,697 B1
DATED         : December 10, 2002
INVENTOR(S)   : George Clark et al.

It is certified that error appears in the above-identified patent and that said Letters Patent is hereby corrected as shown below:

Column 1,
Line 39, "Light" should read -- light --.

Column 6,
Line 28, "formed." should read -- formed --.

Column 8,
Line 28, "has having" should read -- has --.

Signed and Sealed this

Nineteenth Day of August, 2003

JAMES E. ROGAN
*Director of the United States Patent and Trademark Office*